US008574890B2

(12) United States Patent
Icenhour et al.

(10) Patent No.: US 8,574,890 B2
(45) Date of Patent: Nov. 5, 2013

(54) NUCLEIC ACID EXTRACTION FROM COMPLEX MATRICES

(75) Inventors: Crystal R. Icenhour, Charlottesville, VA (US); Brian V. Loyal, Charlottesville, VA (US); Linh N. K. Nguyen, Charlottesville, VA (US)

(73) Assignee: Phthisis Diagnostics Corporation, Charlottesville, VA (US)

( * ) Notice: Subject to any disclaimer, the term of this patent is extended or adjusted under 35 U.S.C. 154(b) by 78 days.

(21) Appl. No.: 13/028,714

(22) Filed: Feb. 16, 2011

(65) Prior Publication Data
US 2011/0201085 A1    Aug. 18, 2011

Related U.S. Application Data

(60) Provisional application No. 61/304,913, filed on Feb. 16, 2010.

(51) Int. Cl.
*C12N 1/08*     (2006.01)
*B01J 20/20*    (2006.01)
*B04B 7/18*     (2006.01)

(52) U.S. Cl.
USPC ............................ 435/270; 502/400; 494/36

(58) Field of Classification Search
None
See application file for complete search history.

(56) References Cited

U.S. PATENT DOCUMENTS 6,129,892 A * 10/2000 Garrett .............................. 422/5
2009/0203004 A1* 8/2009 Sanderson et al. ................ 435/6

FOREIGN PATENT DOCUMENTS

KR   1020090028765 A  *  4/2009
KR   1020090124923 A  * 12/2009

OTHER PUBLICATIONS

Krizman et al., Robust-CTAB-Activated Charcoal Protocol for Plant DNA Extraction, Acta Agric Slovenica, Sep. 1, 2006, vol. 87, No. 2, pp. 427-433.*

SIGMA Dextran Activated Charcoal Data Sheet, Aug. 2006.*
Coconut Shell Activated Carbon from Mexico, Feb. 6, 2005.*
Kim JY, Cho C, Cho BN, J, Plasmid DNA of high quality purified by activated charcoal, Biosci Bioeng. Nov. 2010;110(5):608-13. Epub Jul. 16, 2010.*
Free Online Dictionary, Thesaurus and Encyclopedia.*
Krizman et al., "Robust-CTAB-Activated Charcoal Protocol for Plant DNA Extraction", Acta Agric Slovenica, Sep. 2006, vol. 87, No. 2, pp. 427-433.
Leal-Klevezas et al., "Antifreeze Solution Improves DNA Recovery by Preserving the Integrity of Pathogen-Infected Blood and Other Tissues", Clin Diagn Lab Immunol., Nov. 2000, vol. 7, No. 6, pp. 945-946.
Cricca et al., "Efficient Treatment of Paraffin-Embedded Cervical Tissue for HPV DNA Testing by HC-II and PCR Assays", J. Clin Virol., Feb. 2004, vol. 29, No. 2, pp. 137-140.
Mattingly et al., "Estradiol Stimulates Transcription of Nuclear Respiratory Factor-1 and Increases Mitochondrial Biogenesis", Mol. Endocrinol., Mar. 2008, vol. 22, No. 3, pp. 609-622.
Yaich et al., "Analysis of the PvuII Restriction Fragment-Length Polymorphism and Exon Structure of the Estrogen Receptor Gene in Breast Cancer and Peripheral Blood", Cancer Res., Jan. 1, 1992, vol. 52, No. 1, pp. 77-83.
Kim et al., "A Simple and Rapid Method for Isolation of High Quality Genomic DNA from Fruit Trees and Conifers Using PVP", Nucleic Acids Res., Mar. 1, 1997, vol. 25, No. 5, pp. 1085-1086.
International Search Report mail date Nov. 25, 2011, International Application No. PCT/US2011/025051 filed Feb. 16, 2011.

* cited by examiner

*Primary Examiner* — Christopher M Babic
*Assistant Examiner* — Aaron Priest
(74) *Attorney, Agent, or Firm* — Baker & Hostetler LLP

(57) ABSTRACT

The present disclosure describes an adsorbent and exemplary protocols for extracting nucleic acids, such as DNA and RNA, from complex matrices, such as stool samples and water samples. The adsorbent is activated charcoal coated with a material such as polyvinylpyrrolidone, dextran, or coconut flours. The adsorbent may be used in microcentrifuge spin columns, where it may be present as a slurry in a storage solution. The sample may be prepared by vortexing in a buffer solution, centrifuging, adding a protease to the supernatant, and passing the supernatant through a microcentrifuge spin column containing coated activated charcoal. The key components, including buffer, protease, and spin columns, may be packaged in a kit.

10 Claims, 1 Drawing Sheet

NUCLEIC ACID EXTRACTION FROM COMPLEX MATRICES

CROSS-REFERENCE TO RELATED APPLICATIONS

This application claims priority under 35 U.S.C. §119(e) to provisional U.S. Patent Application No. 61/304,913, filed on Feb. 16, 2010, the disclosure of which is expressly incorporated by reference herein in its entirety.

STATEMENT OF GOVERNMENT INTEREST

The United States Government may own rights in the invention pursuant to grant nos. 1 U01 A1075396-01; 1 NIH 1 R41A1069598-01; and 2 R42 A1069598-02.

BACKGROUND OF THE PRESENT DISCLOSURE

1. Field of the Present Disclosure

The present disclosure is generally directed to a method for purifying total nucleic acids, including DNA and RNA, from specimens such as, e.g., human specimens and environmental samples. Examples of human specimens include, for example purposes only, stool, tissue, urine, and other specimens. Examples of environmental samples include, for example purposes only, water, soil, and other samples. The present disclosure is also applicable to agricultural, veterinary, food, and any other sample from which total nucleic acids samples may be extracted. The present disclosure is more specifically directed to a novel collection of materials and a procedure for use thereof.

2. Related Art

Human stool specimens are typically used in clinical laboratories to diagnose a number of diseases, including colorectal cancer and viral, bacterial, and protozoan infection. In all, it is estimated that over 6.1 million in vitro diagnostic (IVD) tests are performed on stool specimens annually in the United States. Most of these tests use mature technologies such as direct microscopic examination, culture, or immunoassays. However, a growing number of infectious agents, including adenovirus, enterovirus, norovirus, rotavirus, E. coli, and C. difficile, are now identified using molecular methods.

Stool is a complicated matrix that contains a number of proteins, polysaccharides, and small molecules that inhibit the PCR assay at the heart of most molecular assays. Therefore, laboratory staff must isolate the DNA and/or RNA content of a stool specimen prior to molecular analysis. Several commercial products for DNA extraction from stool exist. The most popular of these is the QIAamp Stool DNA Mini Kit, manufactured by Qiagen. This product requires users to process stool specimens through several steps of cell lysis, inhibitor adsorption, and protein digestion before collecting and cleaning the final DNA isolate using a microcentrifuge spin column. The resulting DNA is suitable for most applications. However, the extraction process is long, complicated, and increases the risk of sample cross-contamination. Another alternative is the use of automated DNA extraction instruments, such as the MagNA Pure line of instruments manufactured by Roche Applied Science. However, these instruments require substantial capital investment and additional pre-processing steps for use with stool.

Accordingly, there exists a pressing need for purifying DNA and/or RNA from specimens that is at least one of quicker, less complicated, has reduced capital investment, and requires fewer pre-processing steps.

SUMMARY OF THE PRESENT DISCLOSURE

The present disclosure meets the foregoing need and allows detection of *Cryptosporidium* and *Giardia* species and the like using molecular methods, which results in a significant improvement in speed, sensitivity, reproducibility and other advantages apparent from the discussion herein.

The present disclosure includes a method for purifying total nucleic acids, including DNA and RNA, from human specimens. Other specimen types are contemplated, including, e.g., soil samples, water samples, veterinary samples, agricultural samples, and food samples. The present disclosure includes a novel collection of materials and a procedure for use. The nucleic acid extraction procedure may include two parts:

During the first part, a sample is homogenized in a buffer and clarified by brief centrifugation. A protease enzyme is then used to lyse the suspended cells and degrade any protein PCR inhibitors present in the sample.

During the second part, the digested sample is passed through a microcentrifuge column containing a novel adsorbent. This adsorbent includes an activated charcoal coated with polyvinylpyrrolidone that removes small molecule PCR inhibitors from the sample while allowing purified DNA to flow through the column into a collection tube.

According to one aspect of the present disclosure, a process for extracting nucleic acids from a sample includes homogenizing a portion of the sample in a buffer, centrifuging the homogenized sample to produce a pellet and a supernatant, separating the supernatant from the pellet, adding a protease enzyme to the supernatant, and passing the supernatant over an adsorbent that includes coated activate charcoal.

The sample may be one of a stool sample, a tissue sample, a urine sample, a blood sample, a water sample, a soil sample, an agricultural sample, a veterinary sample, or a food sample. The sample may have a mass of 0.2 g or a volume or 0.2 µL. The supernatant may be incubated. The activated charcoal may be coated with polyvinylpyrrolidone, dextran, or coconut flours. The coated activated charcoal may be present as a slurry of activated charcoal. The weight/volume ratio of the slurry may be from about 5% to about 20%, and the slurry may include from about 1% to about 10% weight/volume of a coating material, which may be one of polyvinylpyrrolidone, dextran, or coconut flours.

According to a further aspect of the present disclosure, a kit for extracting nucleic acids from a sample includes a container of buffer solution, a container of protease enzymes, and one or more spin columns. The spin column contains coated activated charcoal.

The coated activated charcoal may include a slurry of activated charcoal. The activated charcoal may be coated with polyvinylpyrrolidone, dextran, or coconut flours. The weight/volume ratio of the slurry may be from about 5% to about 20%, and the slurry may include from about 1% to about 10% weight/volume of a coating material, which may be one of polyvinylpyrrolidone, dextran, or coconut flours. The buffer solution may be used to homogenize the sample when a portion of the sample is placed in the buffer and vortexed. The coated activated charcoal may be used to bind contaminants while leaving nucleic acids unbound.

According to an additional aspect of the present disclosure, an adsorbent includes a slurry of activated charcoal coated with a coating material. The weight/volume ratio of the slurry may be from about 5% to about 20%, and the slurry may include from about 1% to about 10% weight/volume of a coating material, which may be one of polyvinylpyrrolidone, dextran, or coconut flours. A microcentrifuge column may include the adsorbent in a storage solution. The storage solution may include a weight/volume ratio of the coating material from about 0.1% to about 10%.

Additional features, advantages, and embodiments of the present disclosure may be set forth or apparent from consideration of the following detailed description and claims. Moreover, it is to be understood that both the foregoing summary of the present disclosure and the following detailed description are exemplary and intended to provide further explanation without limiting the scope of the present disclosure as claimed.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and the various ways in which it may be practiced. In the drawings.

DETAILED DESCRIPTION OF THE PRESENT DISCLOSURE

Figure 1:
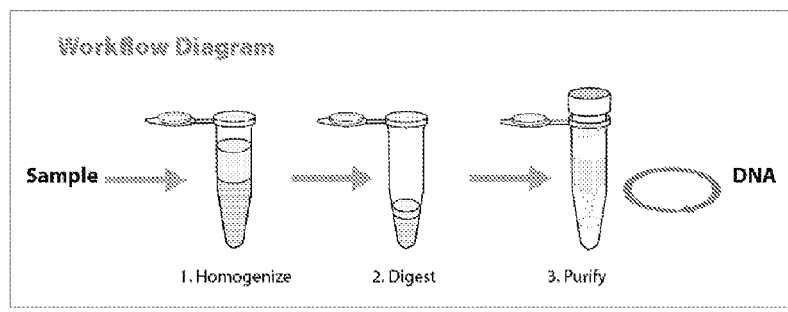
FIG. 1 shows an exemplary workflow of a process for extracting nucleic acids according the present disclosure.

The embodiments of the present disclosure and the various features and advantageous details thereof are explained more fully with reference to the non-limiting embodiments and examples that are described and detailed in the following description. It should be noted that the features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the present disclosure may be practiced and to further enable those of skill in the art to practice the embodiments of the present disclosure. Accordingly, the examples and embodiments herein should not be construed as limiting the scope of the present disclosure, which is defined solely by the appended claims and applicable law.

The nucleic acid extraction procedure may include the following steps:

A sample may be homogenized in a buffer and clarified by brief centrifugation. A protease enzyme may then be used to lyse the suspended cells and degrade any protein PCR inhibitors present in the sample. However, other enzymes are contemplated for use in the present disclosure.

The digested sample may be passed through a microcentrifuge column containing a novel adsorbent. This adsorbent may include an activated charcoal coated with polyvinylpyrrolidone that removes small molecule PCR inhibitors from the sample while allowing purified nucleic acids to flow through the column into a collection tube. Other adsorbents are contemplated and are within the spirit and scope of the present disclosure.

An associated extraction product may be marketed for sale containing the following components:
   One (1) 60-mL bottle containing 25 to 50 mL of buffer
   One (1) microcentrifuge tube containing 100 to 260 µL of enzyme
   One (1) resealable plastic bag containing fifty (50) microcentrifuge spin columns These components may be used in the following exemplary procedure to extract DNA from multiple 0.2 g or µL human stool specimens:
1. Place 0.2 g or 0.2 µL stool samples into microcentrifuge tubes.
2. Add 0.5-mL of buffer to the tubes. Vortex the tubes for 2 minutes or until the sample is completely homogenized.
3. Centrifuge tubes at 200×g for 30 seconds to pellet the solid matter.
4. Transfer 45 µL of each sample supernatant to clean microcentrifuge tubes.
5. Add 5 µL of enzyme to each sample. Mix briefly.
6. Incubate samples at 75° C. for 15 minutes to lyse the cells and digest the protein inhibitors.
7. During the sample incubation, place an appropriate number of spin columns into new microcentrifuge tubes. Centrifuge the columns at 8,000×g for 3 minutes to remove the storage solution. Place the columns into new microcentrifuge tubes.
8. After incubation, transfer the digested samples to the top of the prepared spin columns.
9. Centrifuge the spin columns at 8,000×g for 1 minute, allowing the DNA extract to flow-through to the bottom of the microcentrifuge tubes.

The above-noted times and quantities are exemplary. Other times and quantities may be used together with more or fewer of the above-noted steps as contemplated by the present disclosure.

The buffer and a protease enzyme may be used to lyse the suspended cells and degrade any protein PCR inhibitors present in the sample. The empty microcentrifuge columns and caps may be supplied a third-party vendor.

The adsorbent contained within the microcentrifuge columns may include a 5 to 20% weight/volume (w/v) slurry of activated charcoal (100-400 mesh) in a storage solution. The slurry may be prepared in distilled water containing 0.1 to 10% w/v of HEPES and/or coating materials. Appropriate coating materials include polyvinylpyrrolidone, dextran, coconut flours, and the like.

EXAMPLE 1

Figure 2:
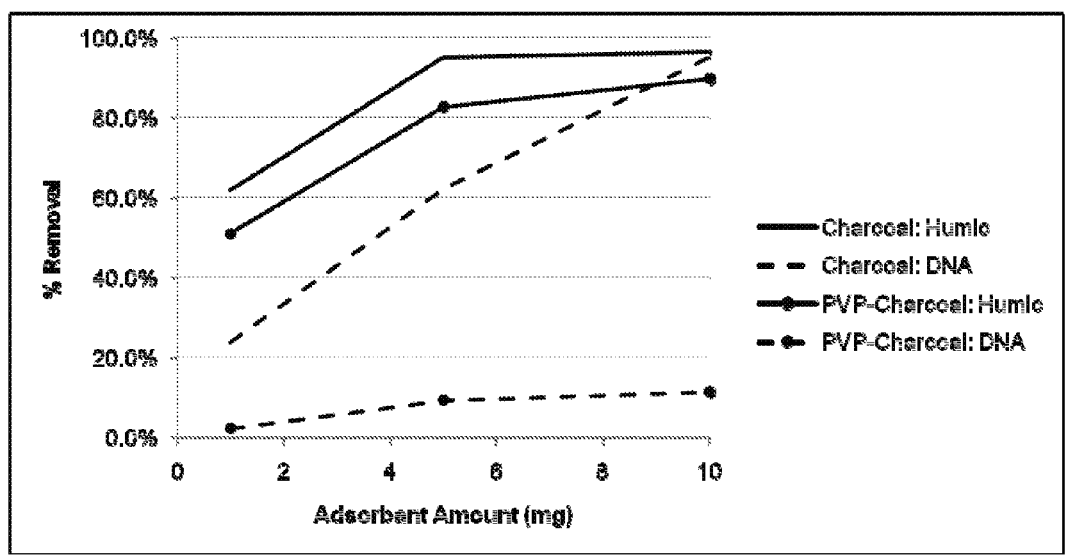
FIG. 2 shows the adsorbency of DNA and humic acid to coated and uncoated activated charcoal.

Polyvinylpyrrolidone was used to coat activated charcoal at 1 to 10% (v/v) and prepared at an appropriate pH ranging from 7.0 to 8.0. The coated activated charcoal binds to contaminants and other PCR inhibitors effectively while leaving the nucleic acid intact and unbound. As shown in FIG. 2, the DNA and humic acid adsorption of uncoated charcoal increases as the amount of charcoal increases. However, when coating activated charcoal with PVP, the humic acid adsorption remains similar to uncoated charcoal while the DNA adsorption decreases.

EXAMPLE 2

The present disclosure was benchmarked against the QIAamp Stool DNA Mini kit using the manufacturer's recommended procedure for microbial DNA extraction. Six 0.2 g human stool samples were spiked with approximately 1×10$^5$ organisms of both *Cryptosporidium parvum* and *Gia-*

*rdia lamblia*. Samples were stored at −20° C. for five months. Three samples were processed using the present disclosure, while the remaining three were processed using the QIAamp method. Purified DNA extracts were analyzed using in-house PCR assays specific for either *Cryptosporidium* or *Giardia* genomic DNA. The following results were obtained:

|  | Present Disclosure | QIAamp |
|---|---|---|
| *Cryptosporidium* yield (Ct) | 30.55 ± 0.50 | 29.96 ± 0.52 |
| *Giardia* yield (Ct) | 26.84 ± 0.62 | 26.00 ± 0.51 |
| Extract Stability (ΔCt) | 0.79 | 0.42 |
| Time for 6 samples (minutes) | 30 | 94 |
| Procedural Steps | 8-10 | 32 |
| Number of Sample Transfers | 2 | 4 |

Reproducibility of both present disclosure and QIAamp were comparable with % $C_V$ less than 10% between 6×$C_t$ values. Extract stability of the present disclosure and QIAamp extracts was tested by obtaining $\Delta C_t$ after −20° C. storage for 2 weeks. There was not any significant difference in extracts obtained using either method.

Note that the DNA yields are provided in terms of PCR cycle threshold ($C_t$) values, indicating the estimated reaction cycle where the fluorescent signal rose above the baseline. Lower $C_t$ values indicate the presence of more target DNA in the sample.

The present disclosure provided equal or better DNA quality and quantity and required fewer steps and less time than the QIAamp method.

EXAMPLE 3

The present disclosure was also tested against an Ambion MagMax-96 Viral RNA kit on a Kingfisher automated platform. Both protocols were used to extract Norovirus RNA in ten clinical stool specimens, and extracts were analyzed by PCR amplification on LightCycler platform.

The following results were obtained:

|  | Kingfisher yield ($C_t$) | Present disclosure yield ($C_t$) | $\Delta C_t$ (Kingfisher-Present disclosure) |
|---|---|---|---|
| V-S-001 | 25.79 | 22.83 | 2.97 |
| V-S-003 | 25.32 | 23.79 | 1.53 |
| V-S-007 | 34.68 | 32.96 | 1.72 |
| V-S-009 | 35.89 | 36.97 | −1.08 |
| V-S-011 | 25.79 | 23.03 | 2.76 |
| V-S-033 | 25.32 | 15.10 | 10.22 |
| V-S-038 | 28.06 | 16.07 | 11.99 |
| V-S-056 | 34.68 | 36.63 | −1.95 |
| V-S-064 | 35.89 | 35.67 | 0.22 |

The present disclosure produced high RNA quality and quantity. In some cases, the present disclosure outperformed the automated Kingfisher extraction method.

EXAMPLE 4

The present disclosure was tested on surface water and wastewater against UltraClean© Soil DNA Isolation kit manufactured by MoBio Laboratories Inc. 10 L and 1 L of water were concentrated via Envirocheck and centrifugation techniques. DNA extractions were performed in replicate for each sample using both the present disclosure and MoBio product separately. Triplicate amplifications were performed per DNA extract using SYBR Green on iCycler (Biorad) platform.

The following results were obtained:

| Sample no. | Description | Volume | Concentration method | $C_T$-value Present disclosure | $C_T$-value MoBio | $\Delta C_t$ (Present disclosure − MoBio) |
|---|---|---|---|---|---|---|
| 1 | Pathumthani water treatment plant, influent, dry season | 10 L | Envirocheck | 37.8 ± 1.4 | 39.2 ± 2.7 | −1.4 |
| 2 | Pathumthani water treatment plant, influent, rainy season | 10 L | Envirocheck | 35.9 ± 2.1 | 40.1 ± 2.5 | −4.2 |
| 3 | Pathumthani water treatment plant, effluent, dry season | 10 L | Envirocheck | no signal | no signal | no signal |
| 4 | Pathumthani water treatment plant, effluent, rainy season | 10 L | Envirocheck | no signal | no signal | no signal |
| 5 | Bangkhen water treatment plant, influent, dry season | 10 L | Envirocheck | 39.3 ± 1.7 | 43.5 ± 1.3 | −4.2 |
| 6 | Bangkhen water treatment plant, influent, rainy season | 10 L | Envirocheck | 37.4 ± 1.9 | 41.3 ± 2.1 | −3.9 |
| 7 | Bangkhen water treatment plant, effluent, dry season | 10 L | Envirocheck | no signal | no signal | no signal |
| 8 | Bangkhen water treatment plant, effluent, rainy season | 10 L | Envirocheck | no signal | no signal | no signal |
| 9 | Canal One surface water (irrigational/municipal) | 10 L | Envirocheck | 32.2 ± 2.3 | 37.8 ± 3.7 | −5.6 |
| 10 | Canal Two surface water (irrigational/municipal) | 10 L | Envirocheck | 36.3 ± 1.5 | 39.7 ± 2.1 | −3.4 |
| 11 | Canal Three surface water (irrigational/municipal) | 10 L | Envirocheck | 37.5 ± 2.5 | 41.6 ± 2.2 | −4.1 |
| 12 | Canal Four surface water (irrigational/municipal) | 10 L | Envirocheck | 35.6 ± 0.9 | 40.5 ± 1.4 | −4.9 |
| 13 | Canal Five surface water (irrigational/municipal) | 10 L | Envirocheck | 39.8 ± 1.1 | 44.3 ± 0.9 | −4.5 |
| 14 | AIT wastewater treatment facility, influent, rainy season | 10 L | Envirocheck | 33.9 ± 2.3 | 39.6 ± 3.2 | −5.7 |
| 15 | AIT wastewater treatment facility, effluent, rainy season | 10 L | Envirocheck | 36.2 ± 1.3 | 42.1 ± 2.2 | −5.9 |
| 16 | AIT main lagoon surface water, rainy season | 10 L | Envirocheck | no signal | no signal | no signal |
| 17 | Canal One surface water, sampling point 1 | 1 L | Centrifugation | 35.1 ± 0.9 | 41.8 ± 3.4 | −6.7 |
| 18 | Canal One surface water, sampling point 2 | 1 L | Centrifugation | 37.7 ± 1.7 | 44.1 ± 0.5 | −6.4 |
| 19 | Canal One surface water, sampling point 3 | 1 L | Centrifugation | 43.1 ± 1.2 | no signal | — |
| 20 | Canal Four surface water, sampling point 1 | 1 L | Centrifugation | 44.4 ± 1.3 | no signal | — |
| 21 | Canal Four surface water, sampling point 2 | 1 L | Centrifugation | 37.8 ± 2.8 | 43.7 ± 1.1 | −5.9 |
| 22 | Canal Four surface water, sampling point 3 | 1 L | Centrifugation | 42.4 ± 0.9 | no signal | — |
| 23 | Canal Premprachakorn surface water, sampling point 1 | 1 L | Centrifugation | 42.5 ± 1.2 | no signal | — |
| 24 | Canal Premprachakorn surface water, sampling point 2 | 1 L | Centrifugation | no signal | no signal | no signal |
| 25 | Canal Premprachakorn surface water, sampling point 3 | 1 L | Centrifugation | no signal | no signal | no signal |

The present disclosure outperformed the MoBio product in both quality and quantity of DNA.

While the present disclosure has been described in terms of exemplary embodiments, those skilled in the art will recognize that the present disclosure can be practiced with modifications in the spirit and scope of the appended claims. These examples given above are merely illustrative and are not meant to be an exhaustive list of all possible designs, embodiments, applications, or modifications of the present disclosure.

What is claimed is:

1. A process for extracting nucleic acids from a sample, the process comprising: homogenizing at least a portion of the sample in a buffer; centrifuging the homogenized sample portion, the centrifugation resulting in a pellet and a supernatant; separating the supernatant from the pellet; adding a protease enzyme to the supernatant; and passing the supernatant over an adsorbent, the adsorbent comprising a slurry of about 5% to about 20% weight/volume activated charcoal in a storage solution, the activated charcoal being coated with a coating material selected from the group consisting of polyvinylpyrrolidone, dextran, and coconut flours.

2. The process of claim 1, wherein the sample is selected from the group consisting of a stool sample, a tissue sample, a urine sample, a blood sample, a water sample, a soil sample, an agricultural sample, a veterinary sample, and a food sample.

3. The process of claim 1, wherein the portion of the sample has at least one of a mass of 0.2 g or a volume of 0.2 µl.

4. The process of claim 1, further comprising incubating the supernatant.

5. The process of claim 1, wherein the slurry comprises from about 1% to about 10% weight/volume of the coating material.

6. A kit for extracting nucleic acids from a sample the kit comprising:
    a container of buffer solution;
    a container of protease enzymes; and
    at least one spin column comprising a slurry of about 5% to about 20% weight/volume coated activated charcoal, wherein the coating material is about 1% to about 10% weight/volume polyvinylpyrrolidone.

7. The kit of claim 6, wherein the buffer solution is configured to homogenize the sample when a portion of the sample is placed in the buffer and vortexed.

8. The kit of claim 6, wherein the coated activated charcoal is configured to bind to contaminant while leaving a nucleic acid unbound.

9. An adsorbent comprising a slurry of about 5% to about 20% weight/volume activated charcoal in a storage solution, the activated charcoal being coated with a coating material selected from the group consisting of polyvinylpyrrolidone, dextran, and coconut flours.

10. A microcentrifuge column comprising the absorbent of claim 9.

* * * * *